(12) United States Patent
Schaller

(10) Patent No.: US 9,364,982 B2
(45) Date of Patent: Jun. 14, 2016

(54) METHOD OF MANUFACTURING AN ILLUMINATED SURGICAL INSTRUMENT

(71) Applicant: NOVARTIS AG, Basel (CH)

(72) Inventor: Philipp Schaller, Stein am Rhein (CH)

(73) Assignee: Novartis AG, Basel (CH)

( * ) Notice: Subject to any disclaimer, the term of this patent is extended or adjusted under 35 U.S.C. 154(b) by 35 days.

(21) Appl. No.: 14/231,903

(22) Filed: Apr. 1, 2014

(65) Prior Publication Data

US 2014/0210116 A1 Jul. 31, 2014

Related U.S. Application Data

(63) Continuation of application No. 13/204,889, filed on Aug. 8, 2011, now abandoned.

(60) Provisional application No. 61/371,882, filed on Aug. 9, 2010.

(51) Int. Cl.
 B29C 45/14 (2006.01)
 A61F 9/007 (2006.01)
 A61B 17/34 (2006.01)

(52) U.S. Cl.
 CPC ....... *B29C 45/14622* (2013.01); *A61F 9/00736* (2013.01); *B29C 45/14598* (2013.01); *A61B 17/3421* (2013.01); *A61F 9/00763* (2013.01)

(58) Field of Classification Search
 None
 See application file for complete search history.

(56) References Cited

U.S. PATENT DOCUMENTS

| 3,089,484 | A | * | 5/1963 | Hett | A61B 1/07 385/107 |
| 3,093,134 | A | * | 6/1963 | Roehr | 604/272 |
| 3,131,690 | A | | 5/1964 | Innis et al. | |
| 3,385,553 | A | * | 5/1968 | Braun | A61M 25/0009 249/142 |
| 3,439,157 | A | | 4/1969 | Myles | |
| 3,910,677 | A | | 10/1975 | Becker et al. | |
| 3,932,022 | A | | 1/1976 | Henning et al. | |
| 3,981,709 | A | | 9/1976 | Kondo et al. | |

(Continued)

FOREIGN PATENT DOCUMENTS

| EP | 0684016 B1 | 12/1999 |
| GB | 1207229 | * 9/1970 |

(Continued)

OTHER PUBLICATIONS

International Searching Authority; International Preliminary Report on Patentability, PCT/US2008/086119, Jul. 20, 2010; 7 pgs.

(Continued)

*Primary Examiner* — Edmund Lee
(74) *Attorney, Agent, or Firm* — Kenneth D. Bassinger

(57) ABSTRACT

An illuminated surgical instrument is disclosed. One embodiment of the illuminated surgical instrument comprises a cannula and an injection-molded light-sleeve adjacent to and encircling at least a portion of the cannula. The surgical instrument can be a vitrectomy probe having a cutting port disposed at a distal end of the cannula. The light-sleeve can terminate near a distal end of the cannula, for example, near the cutting port of the vitrectomy probe. The light-sleeve is optically coupled to a light source. The light-sleeve can be injection-molded during manufacture using the cannula as an insert for the injection molding. The light-sleeve can be oriented for providing illumination in a direction along a longitudinal axis of the instrument.

5 Claims, 2 Drawing Sheets

(56) References Cited

U.S. PATENT DOCUMENTS

| | | | |
|---|---|---|---|
| 4,641,912 A | 2/1987 | Goldenberg | |
| 4,678,268 A | 7/1987 | Russo et al. | |
| 4,693,244 A | 9/1987 | Daikuzono | |
| 4,693,556 A | 9/1987 | McCaughan, Jr. | |
| 4,733,933 A | 3/1988 | Pikulski | |
| 4,781,703 A * | 11/1988 | Walker | A61M 25/0014 604/264 |
| 4,842,390 A | 6/1989 | Sottini et al. | |
| 4,872,837 A * | 10/1989 | Issalene et al. | 433/29 |
| 4,994,047 A * | 2/1991 | Walker | A61L 29/06 600/581 |
| 4,995,691 A | 2/1991 | Purcell, Jr. | |
| 5,037,174 A | 8/1991 | Thompson | |
| 5,351,168 A | 9/1994 | Easley | |
| 5,478,338 A * | 12/1995 | Reynard | A61F 9/00745 606/15 |
| 5,620,639 A * | 4/1997 | Stevens | A61M 5/158 264/504 |
| 5,630,809 A | 5/1997 | Connor | |
| 5,667,472 A | 9/1997 | Finn et al. | |
| 5,860,996 A * | 1/1999 | Urban | A61B 17/3417 604/264 |
| 6,206,823 B1 | 3/2001 | Kolata et al. | |
| 6,387,044 B1 * | 5/2002 | Tachibana | A61B 1/00135 600/114 |
| 6,454,744 B1 * | 9/2002 | Spohn | A61M 25/0668 604/158 |
| 6,939,341 B2 * | 9/2005 | Vijfvinkel | 606/2 |
| 7,766,904 B2 | 8/2010 | McGowan, Sr. et al. | |
| 7,896,838 B2 * | 3/2011 | Devega | 604/116 |
| 7,901,353 B2 * | 3/2011 | Vayser | A61B 1/00135 362/574 |
| 8,496,862 B2 * | 7/2013 | Zelkovich et al. | 264/278 |
| 8,900,139 B2 * | 12/2014 | Yadlowsky et al. | 600/249 |
| 2001/0056278 A1 | 12/2001 | Nield et al. | |
| 2004/0215065 A1 | 10/2004 | Setten | |
| 2005/0080384 A1 * | 4/2005 | Green, Jr. | 604/218 |
| 2005/0135776 A1 | 6/2005 | Vijfvinkel | |
| 2005/0154379 A1 | 7/2005 | McGowan, Sr. et al. | |
| 2006/0135973 A1 * | 6/2006 | Hawkins | A61B 17/3415 606/167 |
| 2007/0179430 A1 * | 8/2007 | Smith et al. | 604/20 |
| 2008/0179792 A1 * | 7/2008 | Kurimoto | B29C 45/1676 264/328.1 |
| 2009/0131931 A1 | 5/2009 | Lee et al. | |
| 2010/0026207 A1 | 2/2010 | Facchini et al. | |
| 2010/0145284 A1 | 6/2010 | Togashi | |
| 2010/0228083 A1 * | 9/2010 | Mirza | A61B 1/00135 600/106 |
| 2010/0228085 A1 * | 9/2010 | Mirza | A61B 1/018 600/106 |
| 2011/0130779 A1 * | 6/2011 | Mirza | A61B 1/018 606/170 |
| 2011/0319839 A1 * | 12/2011 | Del Vecchio | 604/272 |
| 2012/0238830 A1 | 9/2012 | Vukeljic et al. | |
| 2012/0296173 A1 | 11/2012 | Stocks et al. | |
| 2013/0282031 A1 | 10/2013 | Woodard, Jr. et al. | |
| 2014/0100426 A1 * | 4/2014 | Barbour | 600/178 |

FOREIGN PATENT DOCUMENTS

| | | | |
|---|---|---|---|
| JP | 2000245740 A2 | | 9/2000 |
| JP | 2001079010 | | 3/2001 |
| JP | 2009519766 | | 5/2009 |
| JP | 2009148550 | | 7/2009 |
| PL | 166358 | * | 5/1995 |
| WO | 0139705 A1 | | 6/2001 |
| WO | 0248017 A1 | | 6/2002 |
| WO | 2004002337 A1 | | 1/2004 |
| WO | 2008139982 A1 | | 11/2008 |

OTHER PUBLICATIONS

International Searching Authority; International Preliminary Report on Patentability, PCT/US2011/046942, Feb. 12, 2013; 6 pgs.

International Searching Authority; International Search Report, PCT/US2008/086119, Mar. 30, 2009; 2 pgs.

International Searching Authority; International Search Report, PCT/US2011/046942, Nov. 15, 2011; 4 pgs.

International Searching Authority; Written Opinion of the International Searching Authority, PCT/US2008/086119, Mar. 30, 2009; 6 pgs.

International Searching Authority; Written Opinion of the International Searching Authority, PCT/US2011/046942, Nov. 15, 2011; 5 pgs.

* cited by examiner

METHOD OF MANUFACTURING AN ILLUMINATED SURGICAL INSTRUMENT

BACKGROUND OF THE INVENTION

This application is a continuation of U.S. patent application Ser. No. 13/204,889 filed on Aug. 8, 2011, now abandoned which claims priority under 35 U.S.C. §119 to U.S. Provisional Patent Application Ser. No. 61/371,882 filed on Aug. 9, 2010.

The present invention relates to an illuminated surgical instrument, such as a vitrectomy probe or other illuminated ophthalmic surgical instrument, and more particularly to an illuminated surgical instrument having a molded optical light sleeve designed to provide illumination over a specific area at the working end of an instrument, for example, the cutting port of a vitrectomy probe.

Anatomically, the eye is divided into two distinct parts—the anterior segment and the posterior segment. The anterior segment includes the lens and extends from the outermost layer of the cornea (the corneal endothelium) to the posterior of the lens capsule. The posterior segment includes the portion of the eye behind the lens capsule. The posterior segment extends from the anterior hyaloid face to the retina, with which the posterior hyaloid face of the vitreous body is in direct contact. The posterior segment is much larger than the anterior segment.

The posterior segment includes the vitreous body—a clear, colorless, gel-like substance. It makes up approximately two-thirds of the eye's volume, giving it form and shape before birth. It is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free-flowing like the aqueous humor and has normal anatomic attachment sites. One of these sites is the vitreous base, which is a 3-4 mm wide band that overlies the ora serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, called vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions just a millimeter or so in length are made on the sclera at the pars plana. The surgeon inserts microsurgical instruments through the incisions, such as a fiber optic light source to illuminate inside the eye, an infusion line to maintain the eye's shape during surgery, and instruments to cut and remove the vitreous body (such as a vitrectomy probe—which has a cutting end that is inserted into the eye. A vitrectomy probe has a small gauge needle or cannula with a cutting mechanism on the end that is inserted into the eye).

During such surgical procedures, proper illumination of the inside of the eye is important. Typically, a thin optical fiber is inserted into the eye to provide the illumination. A light source, such as a metal halide lamp, a halogen lamp, a xenon lamp, or a mercury vapor lamp, is often used to produce the light carried by the optical fiber into the eye. The light passes through several optical elements (typically lenses, mirrors, and attenuators) and is launched at an optical fiber that carries the light into the eye.

To reduce the number of required incisions during vitrectomy surgery and improve the delivery of light to the surgical site, an effort has been made to integrate a light source (typically one or more optical fibers) with a vitrectomy probe. These efforts have been difficult because of the small diameters of vitrectomy probes. It is desirable to make the diameter of the cutting end of the vitrectomy probe as small as possible so that it can be inserted through very small incisions into the eye.

Traditionally, however, illumination designs consist of many thin diameter round fibers either inserted between an inner and an outer stiff mechanical part or bonded to a tubing component of the surgical instrument. The possible packing density of the optical fibers is limited and it is difficult to handle the thin optical fibers without damage to at least some of them, reducing quality and manufacturing efficiencies. The optical fibers must also have been formed prior to assembly of the surgical instrument. Furthermore, the ends of the optical fibers, which are typically borosilicate glass, must be grinded or polished, which can lead to dust and burrs during manufacture. Manufacturing can thus be time-consuming and expensive.

For example, one prior art illumination system comprises a ring of optical fibers disposed around a vitrectomy probe, or other ophthalmic instrument, and held in place by a sleeve. This illuminated vitrectomy sleeve consists of a bundle of small diameter optical fibers fed into a hub region and then distributed in a ring pattern. The illuminated vitrectomy sleeve is designed to be a stand-alone device into which the vitrectomy probe or other surgical instrument is inserted. As such, it must have its own structural strength that is provided by a sandwiching the array of optical fibers between two metal or plastic cylindrical cannulas. Since it is preferable to make the total diameter of the surgical instrument and sleeve as small as possible, very little cross-sectional area is left to house the optical fibers. Accordingly, very little light is transmitted into the eye.

In another case, a single fiber may be attached to a cannula of a surgical instrument, such as a vitrectomy needle, and held in place with a plastic sleeve. For example, Synergetics, Inc. manufactures a 25-gauge vitrectomy needle with a single optical fiber that is held in place with a plastic sleeve. The plastic sleeve can then fit into a 20-gauge cannula that is inserted into the eye. Very little cross-sectional area is available between the 25 gauge vitrectomy needle and the inner surface of the plastic sleeve (which is typically one or two mils thick). In addition, a larger incision must be made to accommodate the 20-gauge cannula through which the plastic sleeve must fit. Today, it is preferable to keep the incision size small so as to accommodate a probe with a diameter of 23 gauge or smaller. What is needed is an improved illumination system for ophthalmic surgical instruments that can deliver sufficient light into the eye while accommodating these smaller incision sizes.

The same size constraints that apply to the vitrectomy probes of the above examples also restrict the feasible size of other ophthalmic surgical instruments. For example, scissors, forceps, aspiration probes, retinal picks, delamination spatulas, various cannulas, and the like may also benefit from targeted illumination. These instruments are designed to fit through small gauge cannulas that are inserted through the sclera during surgery. The same principles used to design an improved illuminated vitrectomy probe can also be used to provide targeted illumination for these other surgical instruments.

SUMMARY OF THE INVENTION

One embodiment of the present invention is an illuminated surgical instrument comprising: a cannula and an injection-molded light-sleeve adjacent to and encircling at least a portion of the cannula. The surgical instrument can be a vitrectomy probe having a cutting port disposed at a distal end of the cannula. The light-sleeve can terminate near a distal end of the cannula, for example, near the cutting port of the vitrectomy probe. The light-sleeve is optically coupled to a light source. The light-sleeve can be injection-molded during manufacture using the cannula as an insert for the injection molding. The light-sleeve is oriented for providing illumination in a direction along a longitudinal axis of the instrument.

In another embodiment consistent with the principles of the present invention, the present invention is an illuminated surgical instrument. The instrument has a working area located near an end of the instrument. An injection-molded light sleeve terminates near the end of the instrument. The light-sleeve is located adjacent to the instrument. The light-sleeve is optically coupled to a light source. The light-sleeve can be injection-molded during manufacture using a portion of the surgical instrument an insert for the injection molding. The light-sleeve is oriented for providing illumination in a direction along a longitudinal axis of the instrument.

In another embodiment consistent with the principles of the present invention, the present invention is an illuminated surgical instrument. The instrument has a working area located near an end of the instrument. The working area has an orientation with respect to the end of the instrument. An injection-molded light sleeve terminates near the end of the instrument. The light-sleeve is located adjacent to the instrument. The light-sleeve is optically coupled to a light source. The light-sleeve can be injection-molded during manufacture using a portion of the surgical instrument an insert for the injection molding. The light-sleeve is oriented for providing illumination in a direction configured for the orientation of the working area.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
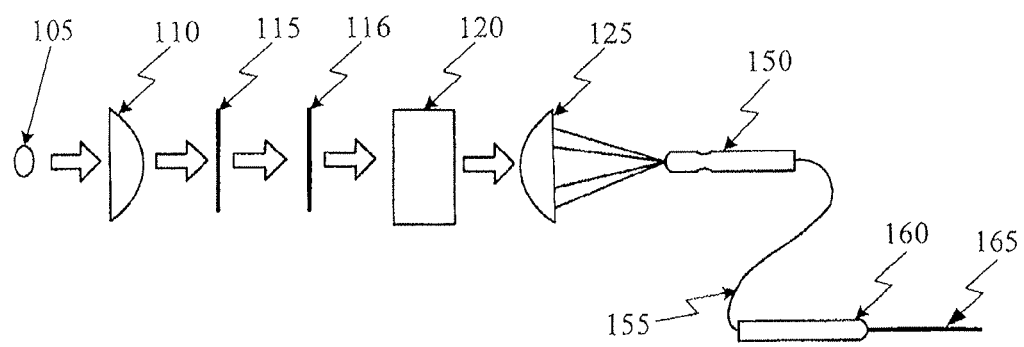
FIG. 1 is an unfolded view of an ophthalmic endoilluminator according to an embodiment of the present invention.

FIG. 1 is an unfolded view of an exemplary illuminated surgical instrument, such as an ophthalmic endoilluminator as used with an illuminated vitrectomy probe, according to an embodiment of the present invention. In FIG. 1, the endoilluminator includes light source 105, collimating lens 110, optional cold mirror 115, optional hot mirror 116, attenuator 120, condensing lens 125, connector 150, optical fiber 155, hand piece 160, and vitrectomy probe 165.

The light from light source 105 is collimated by collimating lens 110. The collimated light is reflected and filtered by optional cold mirror 115 and/or transmitted and filtered by optional hot mirror 116. The resulting beam is attenuated by attenuator 120 and focused by condensing lens 125. The focused beam is directed through connector 150 and optical fiber 155 to vitrectomy probe 165 where it illuminates the inside of the eye as described below.

Light source 105 is typically a lamp, such as a mercury vapor lamp, a xenon lamp, a metal halide lamp, or a halogen lamp. Light source 105 is operated at or near full power to produce a relatively stable and constant light output. In one embodiment of the present invention, light source 105 is a xenon lamp with an arc length of about 0.18 mm. Other embodiments of the present invention utilize other light sources such as light emitting diodes (LEDs). One or more LEDs can be operated to produce a constant and stable light output. As is known, there are many types of LEDs with different power ratings and light output that can be selected as light source 105.

Collimating lens 110 is configured to collimate the light produced by light source 105. As is commonly known, collimation of light involves lining up light rays. Collimated light is light whose rays are parallel with a planar wave front.

Optional cold mirror 115 is a dichroic reflector that reflects visible wavelength light and only transmits infrared and ultraviolet light to produce a beam filtered of harmful infrared and ultraviolet rays. Optional hot mirror 116 reflects long wavelength infrared light and short wavelength ultraviolet light while transmitting visible light. The eye's natural lens filters the light that enters the eye. In particular, the natural lens absorbs blue and ultraviolet light which can damage the retina. Providing light of the proper range of visible light wavelengths while filtering out harmful short and long wavelengths can greatly reduce the risk of damage to the retina through aphakic hazard, blue light photochemical retinal damage and infrared heating damage, and similar light toxicity hazards. Typically, a light in the range of about 430 to 700 nanometers is preferable for reducing the risks of these hazards. Optional cold mirror 115 and optional hot mirror 116 are selected to allow light of a suitable wavelength to be emitted into an eye. Other filters and/or dichroic beam splitters may also be employed to produce a light in this suitable wavelength range. For example, holographic mirrors may also be used to filter light.

Attenuator 120 attenuates or decreases the intensity of the light beam. Any number of different attenuators may be used. For example, mechanical louvers, camera variable aperture mechanisms, or neutral density filters may be used. A variable-wedge rotating disk attenuator may also be used.

Condensing lens 125 focuses the attenuated light beam so that it can be launched into a small diameter optical fiber. Condensing lens 125 is a lens of suitable configuration for the system. Condensing lens 125 is typically designed so that the resulting focused beam of light can be suitably launched into and transmitted by an optical fiber. As is commonly known, a condensing lens may be a biconvex or plano-convex spherical or aspheric lens. In a plano-convex aspheric lens, one surface is planar and the other surface is convex with a precise aspheric surface in order to focus the light to a minimum diameter spot.

The endoilluminator that is handled by the ophthalmic surgeon includes connector 150, optical fiber 155, hand piece 160, and illuminated vitrectomy probe (or other ophthalmic surgical instrument) 165. Connector 150 is designed to connect the optical fiber 155 to a main console (not shown) containing light source 105. Connector 150 properly aligns optical fiber 155 with the beam of light that is to be transmitted into the eye. Optical fiber 155 is typically a small diameter fiber that may or may not be tapered. Hand piece 160 is held by the surgeon and allows for the manipulation of illuminated vitrectomy probe 165 in the eye.

Similarly, a laser light source, such as shown in FIG. 15A, can be optically connected to provide laser light to an endolaser fiber in those embodiments of the illuminated surgical instrument of the present invention that comprise an endolaser fiber to provide laser light to, for example, the retina.

Figure 2A:
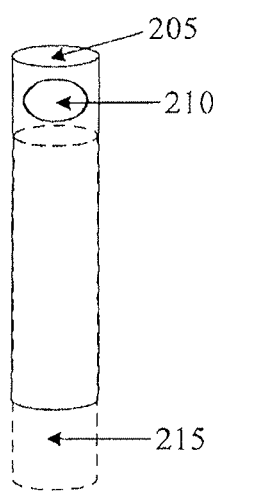
FIGS. 2A and 2B are perspective views of a vitrectomy probe according to an embodiment of the present invention.
Figure 2B:
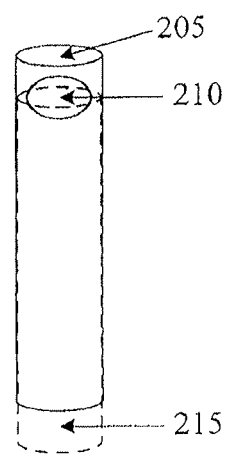

FIGS. 2A and 2B are perspective views of a vitrectomy probe according to an embodiment of the present invention. In a typical vitrectomy probe, an outer cannula 205 includes port 210. An inner piston 215 reciprocates in cannula 205. One end of piston 215 is configured so that it can cut vitreous when as it enters port 210. As shown in FIGS. 2A and 2B, piston 215 moves up and down in cannula 205 to produce a cutting action. Vitreous enters port 210 when the vitrectomy probe is in the position shown in FIG. 2A. The vitreous is cut as piston 215 moves upward closing off port 210 as shown in FIG. 2B. While most of the details of a vitrectomy probe are omitted, it is important to note that the cutting of the vitreous takes place at port 210. Accordingly, it would be desirable to concentrate illumination around port 210, so that a surgeon can see the vitreous being cut (as well as other eye structures near the cutting mechanism).

Figure 3:
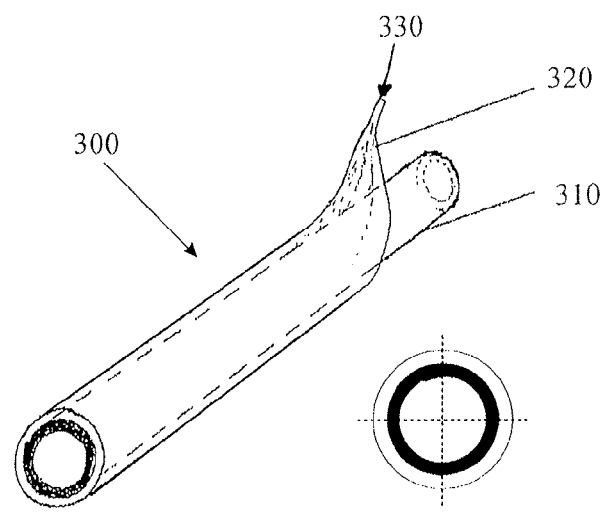
FIG. 3 is a perspective view of an illustrative embodiment of a distal tip portion of an embodiment of an illuminated surgical instrument in accordance with the teachings of the present invention.
Figure 4:
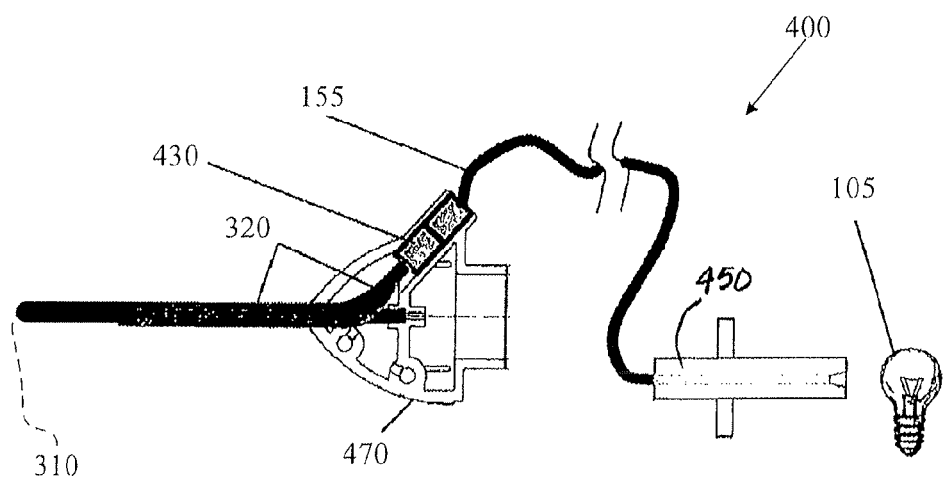
FIG. 4 is a diagrammatical representation of an illustrative embodiment of an illuminated surgical instrument in accordance with the teachings of the present invention.

FIG. 3 is a perspective view of an illustrative embodiment of a distal tip portion 300 of an embodiment of an illuminated surgical instrument in accordance with the teachings of the present invention. FIG. 3 shows a tube 310, which can be, for example, a hollow cannula associated with a number of ophthalmic surgical instruments. Tube 310 can be made of various bio-compatible materials, such as surgical steel, and has a molded light fiber/lightsleeve 320 adjacent to and encircling the outer lateral area of the tube 310. Lightsleeve 320 can be polished at its distal end to provide high light transmission (output) from the lightsleeve 320. Lightsleeve proximal end 330 is optically connected to a light source via, for example, mounting into a ferule and can likewise be polished to provide for high light transmission. Such an arrangement is shown in FIG. 4. Lightsleeve 320 can be injection molded around tube 310 by, for example, injection die-casting. As part of the manufacturing and assembly of an ophthalmic surgical instrument in accordance with the teachings of the present invention, tube 310 can be used as an insert in the injection mold to injection-mold lightsleeve 320 around tube (insert) 310. Lightsleeve 320 can be made from any suitable optically transmissive material capable of being injection-molded, such as polymethylmethacrylate (PMMA).

FIG. 4 is a diagrammatical representation of an illustrative embodiment of an illuminated surgical instrument in accordance with the teachings of the present invention. Illuminated surgical instrument 400 comprises tube 310 around which has been injection-molded lightsleeve 320. Tube 310 and lightsleeve 320 are coupled to distal cap 470 of surgical instrument 400. Distal cap 470 can comprise, for example, the distal cap of a probe handle for holding and manipulating surgical instrument 400, as will be known to those having skill in the art. The proximal end of lightsleeve 320 is optically coupled to a ferule 430 for optically coupling lightsleeve 320 to optical fiber 440. Optical fiber 440 can be a connection cable for coupling the output of light source 460, via an optical coupler 450, to the surgical instrument 400 body (e.g., a probe body). Optical coupler 450 can be standard optical connector and can have identifying technology, such as RFID identification capability, for identifying a particular surgical instrument 400 and configuring surgical instrument 400 for use.

Embodiments of the illuminated surgical instrument of the present invention also include a method of manufacturing a lightsleeve for a surgical instrument, such as lightsleeve 320, using injection-molding techniques. Injection molding of a lightsleeve 320 using the cannula of a surgical instrument as an insert for injection-molding has the advantage over prior art illuminated surgical instruments that the lightsleeve does not have to be formed prior to assembling nor mounted to the cannula in separate processes. The cannula can instead be used as an insert and the lightsleeve injection-molded in an appropriate die.

Other advantages of the various embodiments of the illuminated surgical instrument of the present invention over the prior art include: elimination of the potential risk of uncured adhesives or adhesive inside the cannula as the injection-molding method does not use adhesives to couple the lightsleeve to the cannula; the capability of an inexpensive, simple and fully-automated production process; short production cycle times; highly repeatable production accuracy; the ability to bend a formed cannula and lightsleeve combination to a desired shape without risk of broken light fibers; easy and safe handling of semi-finished instruments; and the ability to define the surgical instrument cannula outer diameter by the design of the injection-molding tooling.

While examples provided herein describe an illuminated vitrectomy probe or other illuminated surgical instrument that can fit through a 23-gauge cannula, it will be appreciated that the same arrangement of a vitrectomy probe and optical fiber array can be applied to cannulas of other sizes. For example, an optical lightsleeve can be arranged around a vitrectomy probe in the same way described herein to fit through a 20-gauge cannula, or even through cannulas smaller than 23-gauge. For example, as the diameter of a vitrectomy probe decreases, more cross section area is available for illumination. An illuminated surgical instrument that fits through a 25-gauge cannula can have the same optical lightsleeve configuration described herein.

More generally, the same principles described with respect to the illuminated vitrectomy probe of the preceding figures can be applied to any surgical instrument designed to fit through a small gauge cannula. For example, in ophthalmic surgery, scissors, forceps, aspiration probes, retinal picks, delamination spatulas, various cannulas, and the like may also benefit from targeted illumination. These instruments are designed to fit through small gauge cannulas that are inserted through the sclera during ophthalmic surgery. For each of these instruments, targeted illumination around the working end of the instrument is beneficial.

The same lightsleeve arrangement can be applied to any surgical instrument with a generally circular, elliptical, rectangular or other cross-section. In this manner, illumination can be targeted to a certain area (typically the working end of the instrument considering the orientation of the instrument in the eye) to provide light where it is needed. For example, in ophthalmic surgery, scissors, forceps, aspiration probes, retinal picks, delamination spatulas, various cannulas, and the like may benefit from targeted illumination. Providing light to the working area of the instrument or to the eye structure with which the instrument interfaces allows the surgeon to better see during surgery.

The same principles can be applied to an instrument of any cross section. In addition, instruments may be approximated by geometrical shapes. For example, an instrument that has an oblong cross section can be approximated by an ellipse. Of course, the location of the targeted illumination corresponds to the location of the distal end of the lightsleeve 320. While the lightsleeve 320 is generally selected to maximize light throughput, its location can be adjusted for a given instrument.

From the above, it may be appreciated that the present invention provides an improved illuminated surgical instrument. Arranging a lightsleeve distal end near the working area of a surgical instrument provides light that is usable by the surgeon during surgery. In addition, the present invention provides a method for effectively injection-molding a lightsleeve around a cannula of an ophthalmic surgical instrument for coupling to a light source and providing illumination to a surgical site. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of manufacturing an illuminated surgical instrument, the method comprising:
   providing a surgical instrument, the surgical instrument comprising a cannula with a length and a diameter; and
   injection molding a light-sleeve adjacent to and encircling the cannula along the entire length of the cannula.

2. The method of claim 1 further comprising:
   optically coupling the light-sleeve to a light source.

3. The method of claim 1 further comprising:
   orienting the light-sleeve for providing illumination in a direction along a longitudinal axis of the surgical instrument.

4. The method of claim 1 further comprising:
   providing a cutting port disposed at a distal end of the surgical instrument.

5. The method of claim 1 wherein injection molding a light-sleeve adjacent to and encircling the cannula along the entire length of the cannula further comprises injection die-casting a light-sleeve adjacent to and encircling the cannula along the entire length of the cannula.

* * * * *